United States Patent
Pierce et al.

(10) Patent No.: US 6,348,616 B1
(45) Date of Patent: Feb. 19, 2002

(54) PRACTICAL SYNTHESIS OF BENZOXAZINONES USEFUL AS HIV REVERSE TRANSCRIPTASE INHIBITORS

(76) Inventors: Michael Ernest Pierce, 3331 Pierson Dr., Wilmington, DE (US) 19810; Lilian Alicia Radesca, 203 Cheltenham Rd., Newark, DE (US) 19711

( * ) Notice: Subject to any disclaimer, the term of this patent is extended or adjusted under 35 U.S.C. 154(b) by 0 days.

(21) Appl. No.: 09/651,793

(22) Filed: Aug. 30, 2000

Related U.S. Application Data

(62) Division of application No. 09/344,250, filed on Jun. 25, 1999, now Pat. No. 6,147,210, which is a continuation of application No. 08/900,016, filed on Jul. 25, 1997, now abandoned.
(60) Provisional application No. 60/022,623, filed on Jul. 26, 1996.

(51) Int. Cl.[7] .............................................. C07C 271/28
(52) U.S. Cl. .......................................... 560/27; 560/30
(58) Field of Search ..................................... 560/30, 27

(56) References Cited

U.S. PATENT DOCUMENTS

| | | | |
|---|---|---|---|
| 5,426,230 A | 6/1995 | Douglas et al. | 564/442 |
| 5,519,021 A | 5/1996 | Young et al. | 514/230.5 |
| 5,608,062 A | 3/1997 | Doller et al. | 544/238 |
| 5,922,864 A | 7/1999 | Frey et al. | 544/92 |

FOREIGN PATENT DOCUMENTS

| | | |
|---|---|---|
| EP | 0582455 | 2/1994 |
| WO | 9314054 | 7/1993 |
| WO | 9520389 | 8/1995 |

OTHER PUBLICATIONS

Tucker et al. (1994) J. Med. Chem., 37: pp. 2437–2444.
Karlsson et al. (1989) Tetrahedron Letters, 30(20): pp. 2653–2656.
Houpis et al. (1994) Tetrahedron Letters, 35(37): pp. 6811–6814.
Hutchins et al. (1973) J. Am. Chem. Soc., 95(11): pp. 3786–3790.
Douglas et al. (1994) Tetrahedron Letters, 35(37): pp. 6807–6810.
Okabe and Sun (1995) Tetrahedron, 51(7): pp. 1861–1866.
Young et al. (1995) Antimicrobial Agents & Chemotherapy, pp. 2602–2605.
Reuter et al. (1994) Tetrahedron Letters, 35(28): pp. 4899–4902.
Reeds et al. (1988) Tetrahedron Letters, 29(45): pp. 5725–5728.
Berger and Kerly (1993) Heterocycles, 36(9): pp. 2051–2058.
Masatomo Iwao (1994) Heterocycles, 38(1): pp. 45–50.
Cho et al. (1991) J. Org. Chem., 56: pp. 7288–7291.

*Primary Examiner*—Richard L. Raymond

(57) ABSTRACT

The present invention describes novel methods for the synthesis of benzoxazinone compounds which are useful as human immunodeficiency virus (HIV) reverse transcriptase inhibitors. The benzoxazinone of the formula:

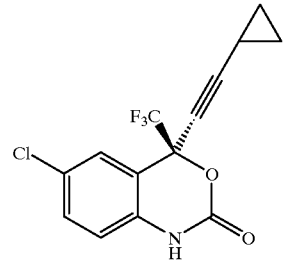

is particularly effective in the treatment of HIV.

2 Claims, No Drawings

PRACTICAL SYNTHESIS OF BENZOXAZINONES USEFUL AS HIV REVERSE TRANSCRIPTASE INHIBITORS

This application is a division of U.S. patent application Ser. No. 09/344,250 filed Jun. 25, 1999, now U.S. Pat. No. 6,147,210, which is a continuation of U.S. patent application Ser. No. 08/900,016 filed Jul. 25, 1997, abandoned, which claims the benefit of U.S. Provisional Application No. 60/022,623 filed Jul. 26, 1996.

FIELD OF THE INVENTION

The present invention relates generally to novel methods for the synthesis of benzoxazinone compounds which are useful as human immunodeficiency virus (HIV) reverse transcriptase inhibitors.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The benzoxazinone of the formula (VI-a):

(VI-a)

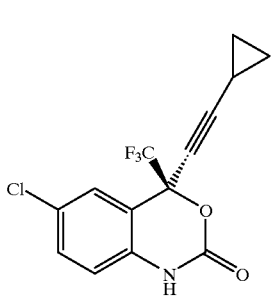

is not only a highly potent reverse transcriptase inhibitor, it is also efficacious against HIV reverse transcriptase resistance. Due to the importance of benzoxazinones as reverse transcriptase inhibitors, synthetic processes for their production need to be developed.

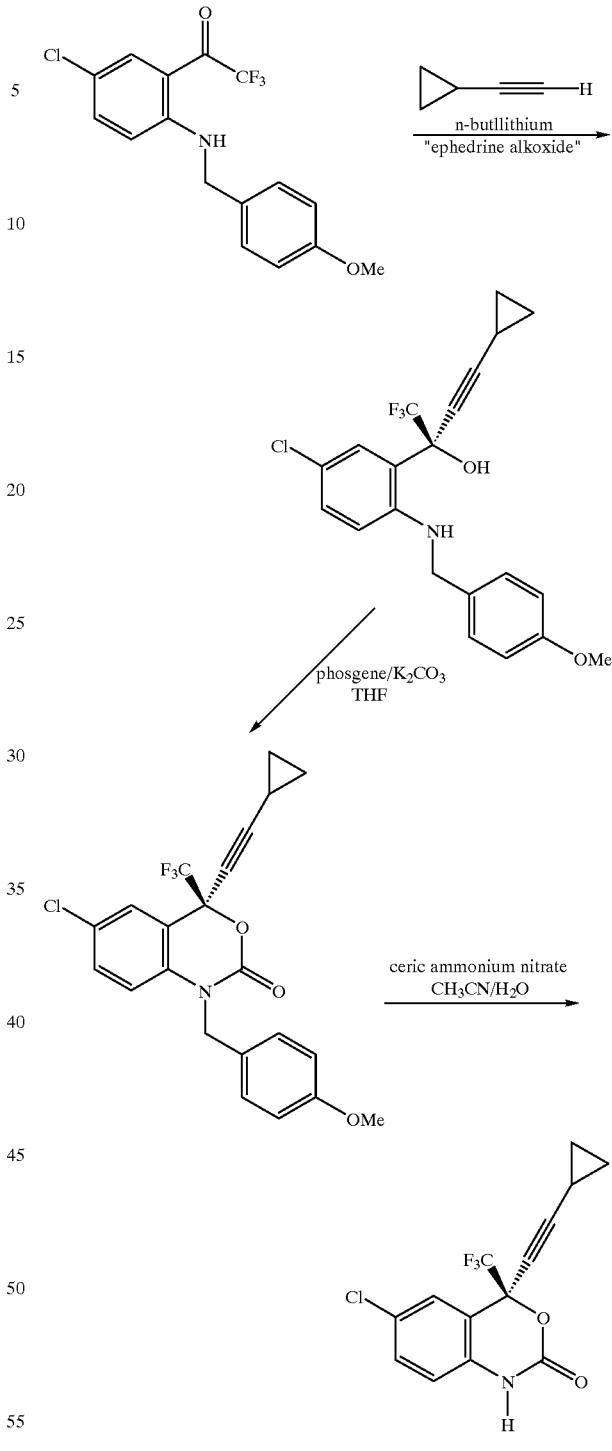

Thompson et al, *Tetrahedron Letters* 1995, 36, 937–940, describe the asymmetric synthesis of an enantiomeric benzoxazinone by a highly enantioselective acetylide addition followed by cyclization with a condensing agent to form the benzoxazinone shown above.

European Patent Application 582,455 A1 describes the synthesis of benzoxazinones via a three step process.

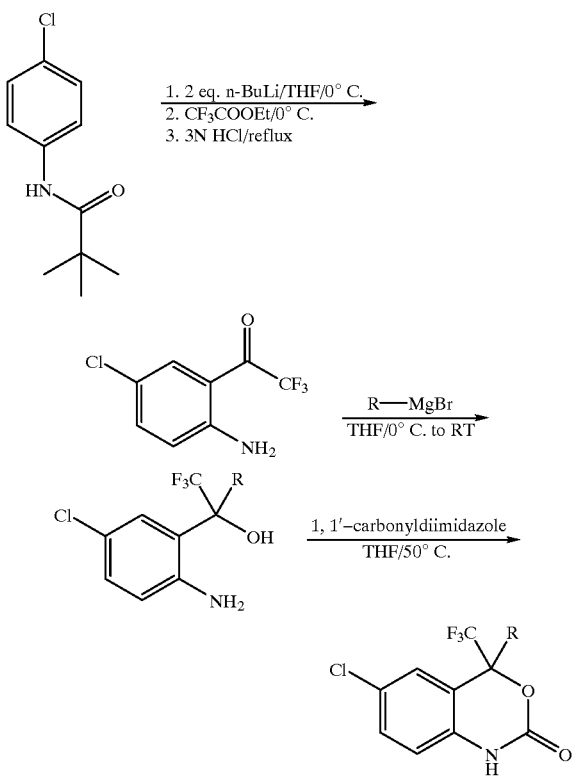

This general method teaches (1) metallation of the pivalamide of parachloroaniline with n-butyllithium followed by nucleophilic substitution with an ester to form a ketone, (2) synthesis of a tertiary carbinol by Grignard addition to the ketone, and (3) cyclization of the unprotected amine with the carbinol by addition of a condensing agent to form a benzoxazinone.

Young et al, PCT International Patent Application Number WO 9520389 A1 describe benzoxazinones useful in the inhibition of HIV reverse transcriptase, the prevention or treatment of infection by HIV and the treatment of AIDS. Application WO 9520389 A1 discloses methods of synthesis which are commensurate with EP 582,455 A1 above. Additionally, Young et al, *Antimicrobial Agents and Chemotherapy* 1995, 39, 2602–2605, in discussing the clinical benefit, the in vitro activity, and the pharmacokinetic activity of benzoxazinone (VI-a) in the treatment of HIV as an HIV reverse transcriptase inhibitor disclose an abbreviated synthesis of benzoxazinone (VI-a) commensurate with EP 582, 455 A1 above wherein the tertiary carbinol is synthesized by addition of a cyclopropyl-ethynyl-lithium reagent before cyclizing the unprotected amine with the carbinol by addition of a condensing agent.

Muchowski and Venuti, *J. Org. Chem.* 1980, 45, 4798–4801, describe the ortho functionalization of N-(tert-butoxycarbonyl)aniline by a corresponding dilithio species using only tert-butyllithium as a practical means of synthesis of ortho-substituted anilines. This reference teaches away from the use of sec-butyllithium and n-butyllithium. The following references describe procedures for ortho lithiation on N-Boc-4-chloro-anilines using tert-butyllithium: Reed et al, *Tetrahedron Letters* 1988, 29, 5725–8; Cho et al, *J. Org. Chem.* 1991, 56, 7288–91; Berger et al, *Heterocycles* 1993, 36, 2051–8; Iwao, *Heterocycles* 1994, 38, 45–50; and Reuter et al, *Tetrahedron Lett.* 1994, 35, 4899–902.

Karlsson et al, *Tetrahedron Letters* 1989, 30, 2653–6, describe a cyclization process for synthesizing five membered cyclic carbamates from an aliphatic N-2-Boc-amino alcohol resulting in a monocyclic oxazolidone.

The formation of benzoxazinones by intramolecular nucleophilic alkoxide ion attack on ethyl and p-nitrophenyl carbamates has been described in the literature for the study of intramolecular enzyme-catalyzed reactions (see Hutchins and Fife, *J. Am. Chem. Soc.* 1973, 95, 3786–90). The rates of ring closure and phenoxide ion release from the ethyl and p-nitrophenyl esters of 2-hydroxymethyl-N-methylcarbanilic acid and 2-hydroxymethylcarbanilic acid were measured in water at 25° under conditions which required excess potassium hydroxide concentrations.

Doller et al, PCT International Application Number WO 93/14054 describes a process for the production of substituted trifluoromethyl ketones of formula (XIV)

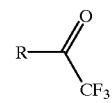

(XIV)

by oxidation of the corresponding substituted trifluoromethyl alcohols.

The above methods for the syntheses of benzoxazinones use toxic, difficult to handle reagents and relatively expensive materials. Thus, it is desirable to discover new synthetic routes to benzoxazinones on a large scale which avoid toxic, difficult to handle reagents and provide high yields of desired benzoxazinones.

Accordingly, the present invention provides an improved synthetic process for the preparation of benzoxazinones. The process of the present invention eliminates use of highly toxic condensing agents such as phosgene and provides for a more efficient intramolecular cyclization using a stoichiometric equivalent of strong base. The present invention eliminates the use of highly toxic ceric ammonium nitrate or replaces messy HCl/EtOH/LiOH for the removal of camphanic acid with a considerably cleaner DMSO/H$_2$O reaction.

The present invention provides novel processes for the addition of cyclopropylethynyl radical to N-Boc-aniline via the cyclopropylethynyl lithium or cyclopropylethynyl trifluoromethyl ketone to produce the carbinol necessary for the intramolecular cyclization reaction.

The present invention provides for intermediates as stable solids purifiable by recrystallization. None of the above-cited references describe the methods of the present invention for the synthesis of benzoxazinones useful as inhibitors of HIV reverse transcriptase.

SUMMARY OF THE INVENTION

The present invention concerns processes for the preparation of benzoxazinone compounds which are useful as HIV reverse transcriptase inhibitors. The processes of the present invention provide high yields, can be conducted on a kilogram scale, and yield stable intermediates. The invention further provides for a facile intramolecular cyclization under mild condition to form benzoxazinone compounds.

There is provided by this invention a process for the preparation of compounds of formula (VI) and derivatives thereof:

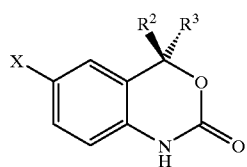

(VI)

wherein X, R², and R³ are as defined below, said process comprising one or more of the following:

(1) (substitution) reacting a compound of formula (I):

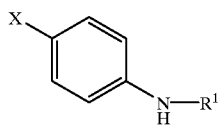

(I)

wherein R¹ is an amine protecting group, which forms a carbamate with the amine,
with sec-butyllithium or another suitable lithiating agent, and ethyl trifluoroacetate in a suitable aprotic solvent, to form a compound of formula (II):

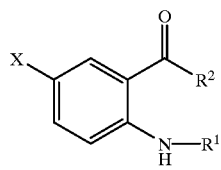

(II)

(2) (addition) reacting a compound of formula (II) with cyclopropylethynyl lithium, which has been generated in situ by the reaction of 5-chloro-1-pentyne with n-butyllithium, in a suitable aprotic solvent, to form a compound of formula (III):

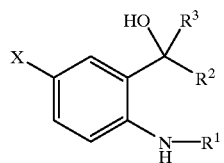

(III)

(3) (cyclization) contacting a compound of formula (III) with n-butyllithium or a suitable strong base, to form a compound of formula (IV)

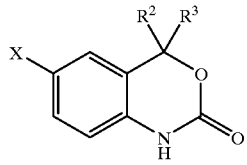

(IV)

(4) (chiral resolution) reacting a compound of formula (IV) with sodium hydride and camphanic acid chloride or a suitable chiral amine protecting group and separating the diastereomers to form a compound of formula (V):

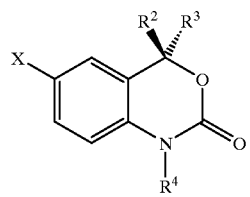

(V)

wherein R⁴ is a chiral amine protecting group, and (5) (nitrogen deprotection) contacting a compound of formula (V) with dimethylsulfoxide and water to form a compound of formula (VI).

DETAILED DESCRIPTION OF THE INVENTION

In a first embodiment, the present invention provides a novel process for the preparation of compounds of formula (IV) and derivatives thereof:

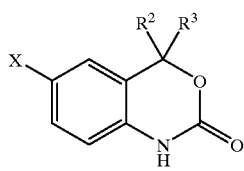

(IV)

wherein:
X is halogen,
R² is trihalomethyl or pentahaloethyl,
R³ is cyclopropylethynyl; said process comprising one or more of the following:

step (1) (nucleophilic substitution)
(a) contacting a compound of formula (I):

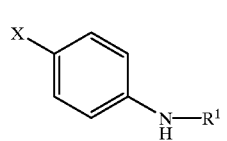

(I)

wherein R¹ is an amine protecting group, which forms a carbamate with the amine,
with a suitable lithiating agent in a suitable solvent, and (b) contacting the resulting compound with an ester of the formula of R²COOR⁵, wherein —OR⁵ is a leaving group, to form a compound of formula (II):

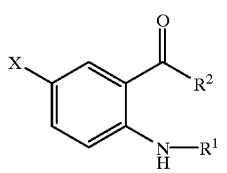

(II)

step (2) (addition)
  (a) contacting 5-halo-1-pentyne with about two equivalents of a suitable metallating agent in a suitable solvent at a temperature sufficient to generate cyclopropylethynyl-M, wherein M is lithium or magnesium halide, in situ; and
  (b) contacting the cyclopropylethynyl-M with a compound of formula (II) in a suitable solvent at a temperature sufficient to form a compound of formula (III):

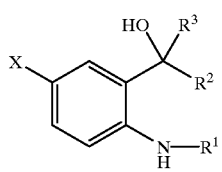
(III)

step (3) (cyclization) contacting a compound of formula (III) with a suitable strong base in a suitable aprotic solvent and heating to a temperature sufficient to form a compound of formula (IV).

In a preferred embodiment:

X is chloro;

$R^1$ is selected from the group consisting of:
  ethoxycarbonyl,
  diisopropylmethoxycarbonyl,
  tert-butyloxycarbonyl,
  menthoxycarbonyl
  bornyloxycarbonyl
  benzyloxycarbonyl,
  cyclopentyloxycarbonyl, and
  adamantyloxycarbonyl;

$R^2$ is trihalomethyl;

$R^3$ is cyclopropylethynyl;

$R^5$ is ethyl;

the suitable lithiating agent is selected from the group consisting of n-butyllithium, sec-butyllithium, and t-butyllithium;

the suitable metallating agent is selected from the group consisting of n-butyllithium, sec-butyllithium, and t-butyllithium; and the suitable strong base is selected from the group consisting of potassium hexamethyldisilazide, sodium hydride, potassium hydride, lithium hydride, n-butyllithium, sec-butyllithium, t-butyllithium, phenyllithium, triphenylmethyllithium, and potassium t-butoxide.

In a more preferred embodiment, the compound of formula (IV) is a compound of formula (IV-a):

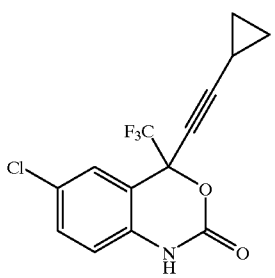
(IV-a)

said process comprises:

step (1) (substitution)
  (a) contacting a compound of formula (I-a):

(I-a)

with about two and one-half equivalents of sec-butyllithium in a suitable aprotic solvent at a temperature of between about −70° C. and −30° C., and (b) adding about one or more equivalents of $F_3CCOOCH_2CH_3$, while maintaining the temperature between about −70° C. and −30° C. to form a compound of formula (II-a):

(II-a)

step (2) (addition)
  (a) contacting about one equivalent of 5-chloro-1-pentyne with about two equivalents of n-butyllithium in a suitable aprotic solvent while maintaining a temperature of between −15° C. and 20° C. to generate cyclopropylethynyl-lithium in situ; and
  (b) contacting about two or more equivalents of said cyclopropylethynyl-lithium with about one equivalent of the compound of formula (II-a) in a suitable solvent at a temperature of between −70° C. and −10° C. to form a compound of formula (III-a):

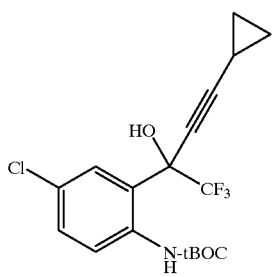

(III-a)

step (3) (cyclization)

contacting the compound of formula (III-a) with about one or more equivalents of n-butyllithium in a suitable aprotic solvent at a temperature of between −70 and 0° C. and heating to a temperature sufficient to effect intramolecular cyclization to form a compound of formula (IV-a).

In the process of the present invention, the intermediates of formula (II) and (III), may optionally be carried through to the next step without isolation of the intermediate, for example, by crystallization or chromatography, between steps in the process.

In a second embodiment, the present invention provides a novel process for the preparation of compounds of formula (IV):

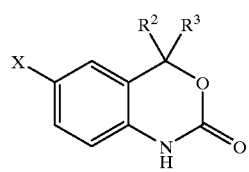

(IV)

wherein

X is halogen, $R^2$ is trihalomethyl or pentahaloethyl, $R^3$ is cyclopropylethynyl; said process comprising:
(a) contacting 5-halo-1-pentyne with about two equivalents of suitable metallating agent in a suitable solvent at a temperature sufficient to generate cyclopropylethynyl-M, wherein M is lithium or magnesium halide, in situ; and
(b) contacting said cyclopropylethynyl-M with a compound of formula (II):

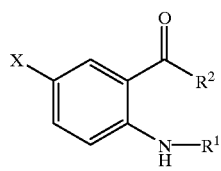

(II)

wherein $R^1$ is an amine protecting group, which forms a carbamate with the amine, in a suitable solvent at a suitable temperature, and
(c) heating to a temperature sufficient to form a compound of formula (IV).

In a third embodiment, the present invention provides a process for the preparation of compounds of formula (III):

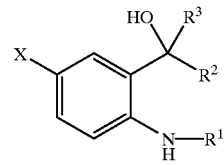

(III)

wherein

X is halogen, $R^1$ is an amine protecting group, which forms a carbamate with the amine, $R^2$ is trihalomethyl or pentahaloethyl, and $R^3$ is cyclopropylethynyl; said process comprising:
(a) contacting a compound of formula (I):

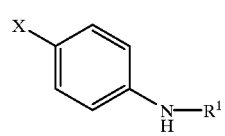

(I)

with a suitable lithiating agent in a suitable aprotic solvent at a suitable temperature; and
(b) contacting the resulting product with a suitable disubstituted ketone of the formula $R^2COR^3$, to form a compound of formula (III).

In a fourth embodiment, the present invention provides a process for the preparation of compounds of formula (IV):

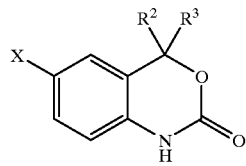

(IV)

wherein

X is halogen, $R^2$ is trihalomethyl or pentahaloethyl, $R^3$ is cyclopropylethynyl; said process comprising:
(a) contacting a compound of formula (I):

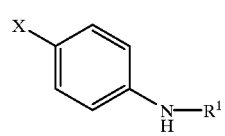

(I)

wherein $R^1$ is an amine protecting group, which forms a carbamate with the amine,
with a suitable lithiating agent in a suitable solvent at a suitable temperature;
(b) contacting the resultant product with a suitable disubstituted ketone of the formula $R^2COR^3$, to form a compound of formula (III); and

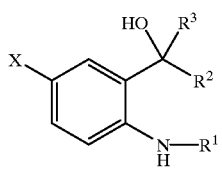

(III)

(c) heating the compound of formula (III) to a temperature suitable to effect intramolecular cyclization to form a compound of formula (IV).

In a fifth embodiment, the present invention provides a process for resolving the racemate of a compound of formula (IV) to produce a stereoisomer of formula (VI):

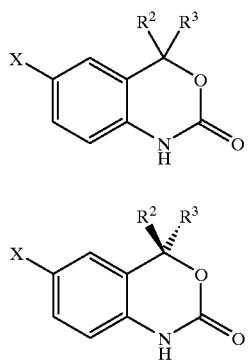

(IV)

(VI)

wherein:
X is halogen,
$R^2$ is trihalomethyl or pentahaloethyl,
$R^3$ is cyclopropylethynyl; said process comprising:
step (1) contacting a compound of formula (IV):

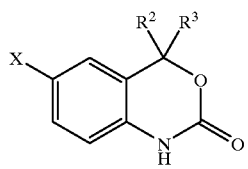

(IV)

with (−)-camphanic acid chloride at a suitable temperature with a suitable base to form a compound of formula (V):

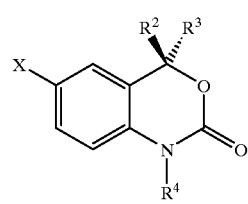

(V)

wherein $R^4$ is the chiral amine protecting group camphanyl,
step (2) separating the compound of formula (V) from the resulting stereoisomers; and step (3) removing the chiral amine protecting group by heating the compound of step (2) in a solution of DMSO and water at a sufficient temperature to effect formation of a compound of formula (VI).

In a sixth embodiment, the present invention provides a novel compound of the formula (II-a):

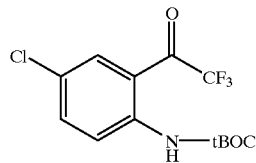

(II-a)

In a seventh embodiment, the present invention provides a novel compound of the formula (III-a):

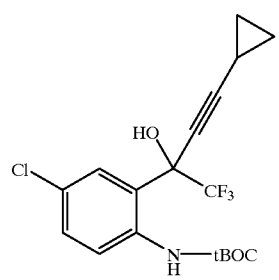

(III-a)

In an eight embodiment, the present invention provides a novel compound of the formula (XV):

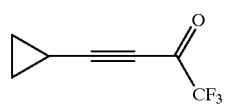

(XV)

In an ninth embodiment, the present invention provides a novel compound of the formula (XVI):

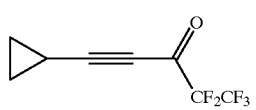

(XVI)

The processes of the present invention are useful for the preparation of benzoxazinones, and compounds which are useful intermediates in the synthesis of benzoxazinones, which are useful as human immunodeficiency virus (HIV) reverse transcriptase inhibitors. Such HIV reverse transcriptase inhibitors are useful for the inhibition of HIV and the treatment of HIV infection. Such HIV reverse transcriptase inhibitors are useful for the inhibition on HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standard or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The following terms and abbreviations are used herein and defined as follows. The abbreviation "THF" as used herein means tetrahydrofuran. The abbreviation "DMSO" as used herein means dimethylsulfoxide. The abbreviation or "DMAC" as used herein means dimethylacetamide. The abbreviation "tBOC" or "BOC" as used herein means t-butyloxycarbonyl. The abbreviation "BuLi" as used herein means butyllithium. The abbreviation "NaH" as used herein means sodium hydride. The abbreviation or "KHMDS" as used herein means potassium hexamethyldisilazide.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable halogenated solvents include chlorobenzene or fluorobenzene.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable basic solvents include: 2-, 3-, or 4-picoline, pyrrole, pyrrolidine, morpholine, pyridine, or piperidine.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene.

As used herein, the term "amine protecting group" (or "N-protected") refers to any group known in the art of organic synthesis for the protection of amine groups which may be reacted with an amine to provide an amine protected by formation of a carbamate. Such amine protecting groups include those listed in Greene and Wuts, "Protective Groups in Organic Synthesis" John Wiley & Sons, New York (1991), the disclosure of which is hereby incorporated by reference. Examples of amine protecting groups include, but are not limited to, the following: 1) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 2) aliphatic carbamate types such as tert-butyloxycarbonyl (Boc), ethoxycarbonyl, diisopropylmethoxycarbonyl, and allyloxycarbonyl; and 3) cyclic alkyl carbamate types such as cyclopentyloxycarbonyl and adamantyloxycarbonyl.

Additional amine protecting groups, which form a carbamate with the amine, may include, but are not limited to, the following: 2,7-di-t-butyl-[9-(10,10-dioxo-10,10,10,10-tetrahydrothio-xanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolyl-methyloxycarbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyl-oxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; and 2-furanylmethyloxycarbonyl.

As used herein, the term "chiral amine protecting group" (or "chiral N-protected") refers to any group known in the art of organic synthesis for the protection of amine groups which may be reacted with an amine to provide an amine protected with a chiral amine protecting group. Such chiral amine protecting groups include those listed in Greene and Wuts, "Protective Groups in Organic Synthesis" John Wiley & Sons, New York (1991), the disclosure of which is hereby incorporated by reference. Examples of chiral amine protecting groups include, but are not limited to, the following: camphanyl, menthyl and borneol.

As used herein, the term "lithiating agent" means any organometallic reagent that can deprotonate the ortho position of compound (I) to yield by substitution with an $R^2$-substituted ester a compound of formula (II). Preferred lithiating agents are, but without limitation, alkyllithium agents. Exemplary lithiating agents include, by way of example but without limitation: n-hexyllithium, n-octyllithium, n-butyllithium, t-butyllithium, sec-butyllithium, and isobutyllithium.

As used herein, the term "metallating agent" means any organometallic reagent that can effect the formation of a compound of the formula $R^3$-M, wherein M is lithium or magnesium halide and add a $R^3$-substituent to the carbonyl of compound (II) to yield a compound of formula (III). Preferred metallating agents are, but without limitation, lithium hydride, alkyllithium agents and Grignard reagents such as alkylmagnesium halides and arylmagnesium halides. Exemplary metallating agents include, by way of example but without limitation: n-butyllithium, sec-butyllithium, t-butyllithium, ethylmagnesium bromide, and phenylmagnesium bromide.

As used herein, the term "strong base" means any organometallic reagent, metal hydride or metal alkoxide that can effect by intramolecular cyclization the formation of compound (IV) from a compound of formula (III). Preferred strong bases are, but without limitation, potassium hexamethyldisilazide, sodium hydride, potassium hydride, lithium hydride, potassium t-butoxide, phenyllithium, triphenylmethyllithium, and alkyllithium agents. Exemplary alkyllithium agents include, by way of example but without limitation: n-butyllithium, sec-butyllithium, and t-butyllithium.

As used herein, the term "leaving group" (or —OR$^5$) refers to any group known in the art of organic synthesis which cleaves from a substrate ester upon addition of the ester carbonyl group to another nucleophile. Such leaving groups, wherein R$^5$ is an alkyl or a carbocyclic group, can include, but are not limited to, methoxy, ethoxy, propoxy, butoxy, pentoxy, phenoxy, and benzyloxy.

"Halo" or "halogen" as used herein refers to fluoro, chloro and bromo.

"Alkyl" as used herein is intended to include both branched and straight chain saturated aliphatic hyrdocarbon groups having one to twelve carbon atoms. "Carbocyclic" or "carbocycle" as used herein is intended to include any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Scheme 1. Scheme 1 details the general synthetic method for preparation of compounds of formula (IV).

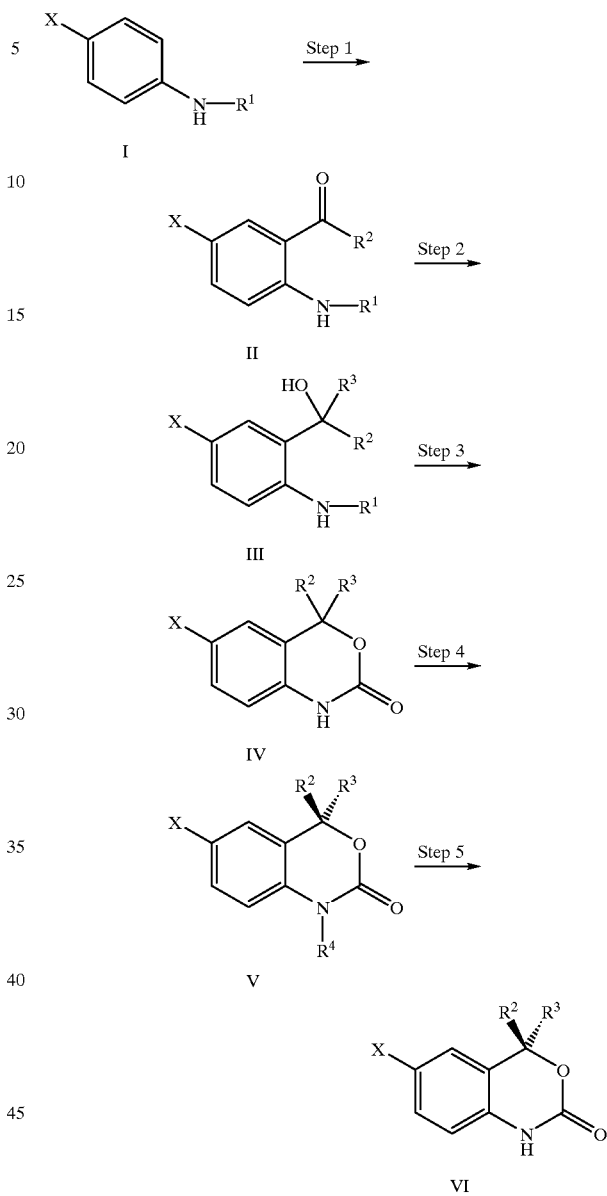

It is the object of the present invention to provide an improved process for the preparation of benzoxazinones which are useful as HIV reverse transcriptase inhibitors.

Step 1: Substitution: Preparation of Compound of Formula (II)

This step is conducted by reacting a compound of formula (I) in a suitable solvent at a suitable temperature with at least about two molar equivalents of a lithiating agent for a suitable length of time, followed by treatment of the activated lithiated intermediate with preferably at least about one molar equivalent, more preferably about two molar equivalents, of an ester of formula R$^2$COOR$^5$, to form a compound of formula (II). By way of general guidance, compound (I) in an aprotic solvent at a temperature below −30° C. may be contacted with 2–3 molar equivalents of a lithiating agent for 1–2 hours followed by treatment in situ of the resulting activated lithiated intermediate with 1–3 molar equivalents of an $R^2COOR^5$ ester at a temperature below −30° C. for 0.1–2 hours to form compound (II). Compound (II) may be separated from the reaction as a stable solid by quenching with a suitable agent, preferably t-butyl methyl ether, followed by standard methods of work up. An example of standard work up is shown in Example 1. Optionally, compound (II) may be carried forward in synthesis of compounds of formula (III) and (IV).

$R^1$ is an amine protecting group, which forms a carbamate with the amine, and is preferably tert-butyloxycarbonyl or ethoxycarbonyl.

Preferred lithiating agents for step (1) include n-butyllithium, sec-butyllithium, t-butyllithium, n-hexyllithium and iso-butyllithium. A more preferred lithiating agent is sec-butyllithium.

Preferred solvents and mixtures thereof for step (1) are tetrahydrofuran and cyclohexane.

A preferred reaction time for step (1) following addition of the lithiating agent is about one hour and following addition of the ester is about 30 minutes.

A preferred temperature range for step (1) is about −35 to −45° C.

Step 2: Addition: Preparation of Compound of Formula (III)

This step comprises the alkylation of the ketone carbonyl of a compound of formula (II) in a suitable solvent with preferably at least about one equivalent of a cyclopropylethynyl lithium, said cyclopropylethynyl lithium being generated in situ for the addition of an $R^3$ substituent to compound (II), for a suitable length of time at a temperature sufficient to form a compound of formula (III). Generation of about three equivalents of cyclopropylethynyl lithium in situ may be carried out by contacting about three equivalents of 5-halo-1-pentyne with about six equivalents of a suitable metallating agent in a suitable solvent at a temperature below 10° C. for 1–3 hours. Upon sufficient formation of cyclopropylethynyl lithium, about one equivalent of compound of formula (II) in a suitable solvent is added and maintained at a temperature below −30° C. for 1–3 hours to form compound (III). Compound (III) may be separated from the reaction as a stable solid by standard methods of work up. An example of standard work up is shown in Example 2. Optionally, compound (III) may be carried forward in synthesis of compounds of formula (IV).

Preferred 5-halo-1-pentynes for step (2) include 5-bromo-1-pentyne and 5-chloro-l-pentyne.

Preferred metallating agents for step (2) include n-butyllithium, sec-butyllithium, t-butyllithium, iso-butyllithium, n-hexyllithium and octyllithium. A more preferred metallating agent is n-butyllithium.

Preferred solvents and mixtures thereof for step (2) are tetrahydrofuran, hexane and methyl t-butylether.

Preferred reaction times in step (2) are about two hours for generation of cyclopropylethynyl lithium and about 1.5–2 hours for addition of cyclopropylethynyl lithium to compound (II).

Preferred temperature ranges for step (2) are about −5 to 5° C. for generation of cyclopropylethynyl lithium and about −70 to −10° C. for addition of cyclopropylethynyl lithium to compound (II).

Step 3: Cyclization: Preparation of Compound of Formula (IV)

This step comprises reacting a carbinol compound of formula (III) in a suitable solvent with preferably at least about one equivalent of a suitable strong base at a sufficient temperature for a suitable length of time to form a compound of formula (IV). By way of general guidance, compound (III) in an aprotic solvent at a temperature below 20° C. may be contacted with about one molar equivalent of a strong base and heated to a temperature for 2–6 hours sufficient to form compound (IV). Compound (IV) may be separated from the reaction as a stable solid by quenching with a suitable aqueous acid, followed by standard methods of work up. An example of standard work up is shown in Example 3.

Preferred strong bases for step (3) include n-butyllithium, sec-butyllithium, t-butyllithium, n-hexyllithium, and sodium hydride. A more preferred strong base is n-butyllithium.

Preferred solvents and mixtures thereof for step (3) are toluene, hexane and tetrahydrofuran.

Reaction times for step (3) depend on the solvent and temperature. A preferred reaction time for step (3) when the solvent is toluene following addition of the strong base is about four hours.

A preferred temperature range for the addition of strong base to compound (III) in step (3) is about 0–40° C.

Step 4: Nitrogen Protection: Preparation of Compound of Formula (V)

This step comprises the reaction of a racemic benzoxazinone compound of formula (IV) in a suitable solvent with a chiral amine protecting group. By way of general guidance, compound (IV) in an aprotic solvent may be contacted in alternating multiple additions with a total of about three equivalents of a suitable base, preferably sodium hydride or KHMDS, and a total of about 1.5 equivalents of a chiral amine protecting group at a sufficient temperature for a suitable length of time to form a compound of formula (V). Compound (V) may be separated from the reaction as a stable solid by quenching with a suitable aqueous acid, preferably acetic acid, followed by chromatography and standard methods of work up. An example of standard work up is shown in Example 4.

Preferred $R^4$ chiral amine protecting groups for step (4) include camphanyl, menthyl and borneol. Most preferably the chiral amine protecting group is camphanyl.

Preferred solvent for step (4) is tetrahydrofuran.

Preferred reaction time for step (4) is about eight hours.

A preferred temperature range for the addition of base and chiral amine protecting group to compound (IV) in step (4) is about 0–30° C.

Step 5: Nitrogen Deprotection: Preparation of Compound of Formula (VI)

This step comprises deprotection of the chiral amine protecting group, $R^4$, on an isomericaly pure benzoxazinone compound of formula (V) in a suitable solvent by heating to sufficient temperature for a sufficient length of time to form a compound of formula (VI). Compound (VI) may be separated from the reaction as a stable solid by standard methods of work up. An example of standard work up is shown in Example 5.

Preferred solvents in step (4) are the mixtures of DMSO/$H_2O$ or DMAC/$H_2O$ in the ratio of 4/1. Most preferably the solvent mixture is DMSO/$H_2O$.

Preferred reaction time for step (4) is about six hours.

Preferred temperature range in step (4) is about 100–110° C.

The present invention may be further exemplified by, without being limited to, reference to Scheme 2.

With a judicious selection of reagents, as is well appreciated to one skilled in the art of organic synthesis, the claimed process can be performed in a straightforward manner to yield the compounds of formulas (II), (III), (IV), (V) and (VI).

Scheme 2

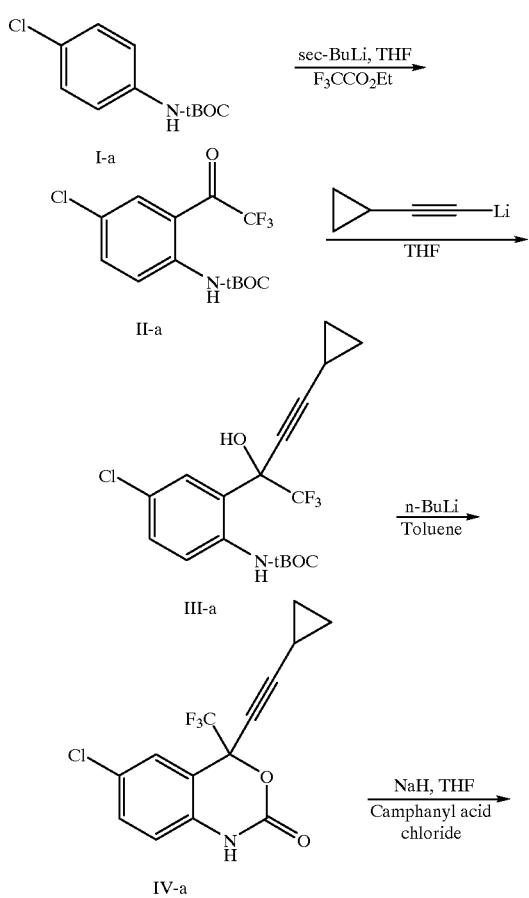

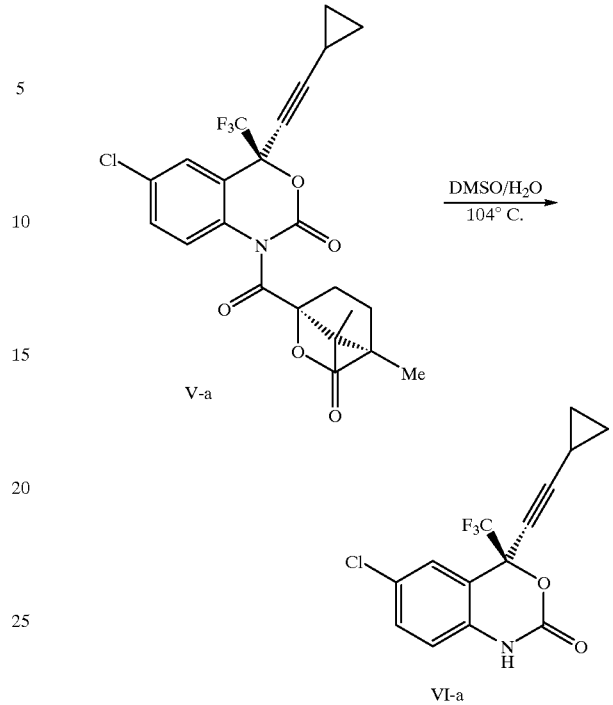

The methods of the present invention, by way of example and without limitation, may be further understood by reference to Scheme 3. This scheme details further embodiments of the general synthetic method for preparation of compounds of formula (IV) utilizing carbamate and carbinol substituents to accomplish benzoxazinone formation by intramolecular cyclization.

Scheme 3

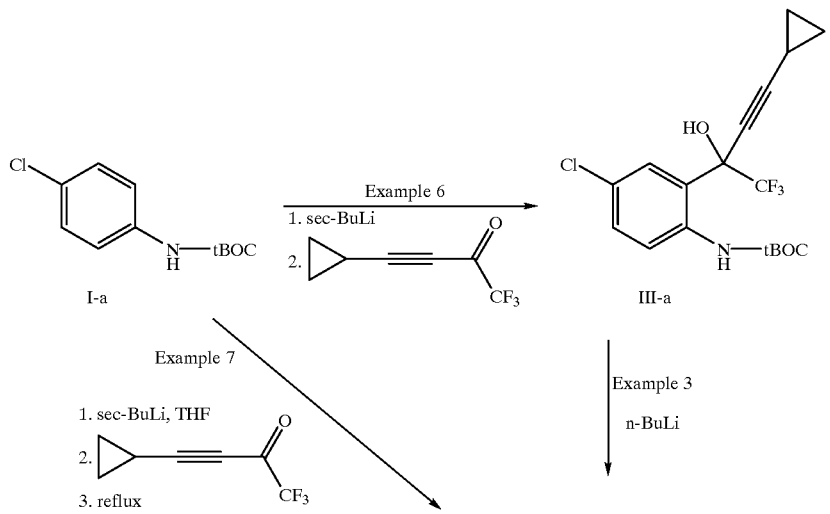

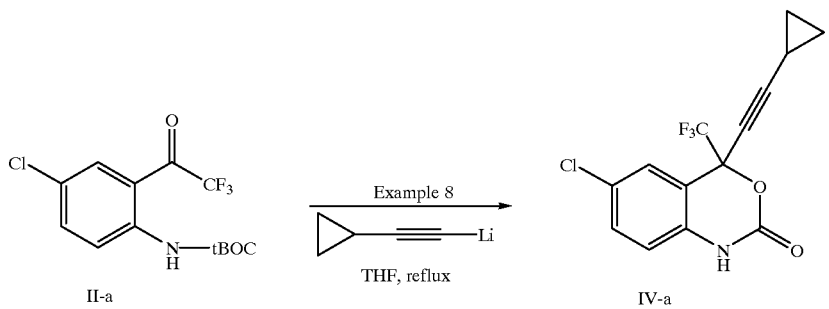

Each of the references cited herein are hereby incorporated herein by reference.

The following examples are meant to be illustrative of the present invention. These examples are presented to exemplify the invention and are not to be construed as limiting the invention's scope.

EXAMPLE 1

Scheme 2, Synthesis of II-a from I-a.

N-t-BOC-4-chloroaniline (Compound I-a) (495 g, 2.18 moles) was dissolved in 2.5 liters of anhydrous THF. The solution was cooled down to −50° C. sec-Butyllithium, 12 weight % in cyclohexane (2.91 Kg, 5.44 moles), was then added at a rate that the pot temperature was −40° C. The pot temperature was held between −39 and −42° C. for 1 hour and then was cooled to −60° C. Ethyl trifluoroacetate (773 grams, 5.44 moles) was added at a rate that the temperature was below −40° C. The reaction mixture was then held at −39 to −42° C. for 30 minutes. The reaction was quenched with 3.75 liters of t-butyl methyl ether and 4.4 liters of 5% aqueous solution of acetic acid. Layers were separated. The organic layer was washed twice with 3.75 liters of 7.5% sodium chloride solution. The organic solution was concentrated in vacuo to a volume of approximately 2 liters. Solvent exchange to acetonitrile was done by adding 1.5 liters of acetonitrile twice and concentrating the crude to a yellow paste. 500 mL of acetonitrile was then added and the mixture was warmed up to 45° C. until dissolution was complete. Then it was slowly cooled down to −20° C. and held for 15 minutes. The solids were filtered and the cake was washed with cold (−20° C.) acetonitrile. After drying at 35° C. in a vacuum oven, 539.9 g of compound II-a was obtained (76% yield). mp 74.5–76.0° C.; $^1$H NMR (CDCl$_3$) d 10.20 (bs, 1H), 8.58 (d, J=9.11 Hz, 1H), 7.86 (m, 1H), 7.60 (dd, J=9.11, 2.28 Hz, 1H), 1.54 (s, 9H); $^{13}$C NMR (CDCl$_3$) d 181.73, 152.26, 143.13, 137.26, 130.72, 126.49, 121.19, 116.33, 115.54, 81.90, 28.16 (triple intensity); $^{19}$F NMR (CDCl$_3$) d −70.2; IR (cm$^{-1}$) 3321, 2987, 1731, 1688, 1577, 1515, 1397, 1261; HRMS calcd. for C$_{13}$H$_{13}$ClF$_3$NO$_3$ 323.0536, found 323.0513; Anal. calcd. for C$_{13}$H$_{13}$ClF$_3$NO$_3$ C 48.22, H 4 .02, Cl 10.97, F 17.62, N 4.33, found C 48.36, H 3.90, Cl 10.44, F 17.67, N 4.26.

EXAMPLE 2

Scheme 2, Synthesis of III-a from II-a.

Anhydrous THF (3.5 liters) was added to n-butyllithium 2.5M (2.55 liters, 11.38 moles) precooled to −14° C. at a rate that the pot temperature was below 5° C. The mixture was cooled to −17° C. and 5-chloro-1-pentyne (550 g, 5.25 moles) was added at a rate that the pot temperature was between 0 and 5° C. The mixture was held at 0° C. for 2 hours, then it was cooled down to −5° C. and diisopropylamine (107 g, 1.05 moles) was added and stirred for 10 minutes. The mixture was then cooled to −45° C. and a solution of Compound II-a (556 g, 1.75 moles) in THF (725 mL) was slowly added to keep the pot temperature below −35° C. After 1 h 45 minutes, the reaction was quenched with isopropyl alcohol (684 g, 11.38 moles) at −40° C. NH4OH, saturated solution (2.6 liters) and t-butyl methyl ether (2.6 liters) was added and stirred for 10 minutes. Layers were separated. The top organic layer was washed with brine (2.6 liters) for 10 minutes. Layers were separated. The mixture was concentrated in vacuo to a volume of 3.5 liters. Heptane (3.5 liters) was added. The mixture was concentrated to a volume of 3 liters. Heptane (3.5 liters) was added. The mixture was concentrated to a volume of 2.2 liters. Heptane (1.75 liters) was added. The mixture was concentrated to a volume of 2.6 liters. The product precipitated and the slurry was cooled to 10° C. and it was stirred overnight at 10° C. The solids were filtered and the cake was washed with heptane (1.75 liters) at 10° C. 440 grams of Compound III-a was obtained, 65% yield. mp 153–156° C.; $^1$H NMR (CDCl$_3$) d 8.36 (bs, 1H), 7.98 (d, J=8.7 Hz, 1H), 7.67 (m, 1H), 7.31 (dd, J=8.7, 2.3 Hz), 1.56 (S, 9H), 1.38 (m, 1H), 0.94–0.82 (m, 4H); $^{13}$C NMR (DMSO-d$_6$) d 151.99, 137.25, 129.82,129.12, 125.87, 124.48, 123.69, 122,58, 93.81, 80.02, 73.54, 69.74, 27.84 (triple intensity), 8.25, 8.19, −1.19; $^{19}$F NMR (CDCl$_3$) d −80.4; IR (cm$^{-1}$) 3359, 2974, 2243, 1688, 1583, 1502, 1390, 1292, 1254, 1165; HRMS calcd. for C$_{18}$H$_{19}$ClF$_3$NO$_3$ 389.1006, found 323.1004; Anal. calcd. for C$_{18}$H$_{19}$ClF$_3$NO$_3$ C 55.46, H 4.88, Cl 9.11, F 14.63, N 3.59, found C 55.69, H 4.99, Cl 9.34, F 14.21, N 3.47.

EXAMPLE 3

Scheme 2, Synthesis of IV-a from III-a.

Compound III-a (450 g, 1.155 moles) was dissolved in 2.2 liters of toluene. The solution was cooled down to 0–4° C. n-Butyllithium, 2.5 molar in hexane (462 mL, 1.155 moles) was added to the mixture at a rate that the temperature was below 20° C. After addition was complete, the mixture was heated to reflux. After 4 hours, the reaction mixture was allowed to cool to room temperature and it was quenched with 2.2 liters of 5% aqueous acetic acid solution and 2.2 liters of t-butyl methyl ether. Layers were separated. The organic layer was washed twice with 10% sodium chloride solution. Then it was concentrated in vacuo to a thick white paste. Heptane (2.2 liters) was added and cooled to 0–4° C. for 2 hours. The solids were filtered and the cake was washed with 1 liter of precooled (−20° C.) heptane. The solids were dried in the vacuum oven at 40° C. to yield 324.8 g (89% yield) of Compound IV-a. mp 183–186° C.; $^1$H NMR (CDCl$_3$) d 9.66 (s, 1H), 7.49 (bs, 1H), 7.36 (dd, J=8.7, 2.3 Hz, 1H), 6.88 (d, J=8.7 Hz, 1H), 1.40 (m, 1H), 0.97–0.83 (m, 4H); $^{13}$C NMR (DMSO-d$_6$) 146.28, 134.74, 132.05, 126.97, 126.61, 122.27, 116.85, 114.10, 95.62, 77.66, 65.88, 8.49, 8.46, −1.29; $^{19}$F NMR (CDCl$_3$) d −81.5; IR (cm$^{-1}$) 3316, 3094, 2250, 1752,1602, 1498, 1196, 1186; HRMS calcd. for C$_{14}$H$_9$ClF$_3$NO$_2$ 315.0274, found 315.0270; Anal. calcd. for C$_{14}$H$_9$ClF$_3$NO$_2$ C 53.25, H 2.85, Cl 11.25, F 18.07, N 4.44, found C 53.67, H 2.98, Cl 11.11, F 17.69, N 4.27.

EXAMPLE 4
Scheme 2, Synthesis of V-a from IV-a.

Sodium hydride (96.6 g, 4.025 moles) was added to 3.95 liters of THF. Compound IV-a (563.7 g, 1.7867 moles) was then charged and stirred for 15 minutes. Camphanic acid chloride (434.4 g, 2.006 moles) was added and stirred for 2 hours. More sodium hydride (11.3 g, 0.4708 moles) was charged and then camphanic acid chloride (79.0 g, 0.3649 moles). After 4 hours temperature was raised to 28° C. and stirred for 50 minutes. Sodium hydride (14.3 g, 0.5955 moles) and camphanic acid chloride (79 g, 0.3648 moles) extra was charged and stirred for 1 h 20 minutes. The reaction was quenched with 1.8 liters of ethyl acetate and 3.6 liters of 1N acetic acid at a rate that the temperature was below 20° C. It was stirred for 10 minutes. Layers were separated. Saturated sodium bicarbonate solution (1.8 liters) was added to the organic layer and stirred for 15 minutes. Layers were separated. The organic layer was concentrated in vacuo to a thick oil. Toluene (1.8 liters) was added and the solution was divided in two portions. Each portion was concentrated to a thick oil and chromatographed on silica gel using toluene as the eluent solvent to separate the desired diastereomer. All the desired fractions were combined and concentrated to a thick oil. Heptane (0.98 liters) was added and it was concentrated to a thick oil. Heptane (0.98 liters) was added and it was concentrated to a thick oil. Heptane (0.98 liters) addition was repeated once. Heptane:ethyl acetate (93:7, 8.2 liters) was then added and heated to 70–800° C. and the temperature was held for 1 h 40 minutes. The heat was the shut off and it was allowed to cool slowly overnight. The solid was filtered and the cake was washed with heptane:ethyl acetate (93:7, 0.8 liters) three times. The solid was dried at 35° C. in a vacuum oven until constant weight to yield 299.6 g (34% yield) of Compound V-a.

EXAMPLE 5
Scheme 2, Synthesis of VI-a from V-a.

Compound V-a (294 g, 0.5933 moles) was dissolved in DMSO (1.8 liters) at 40° C. Water (450 mL) was added and the mixture was heated to 104° C. After 5.5 hours heat was turned off and it was allowed to reach room temperature. The mixture was filtered, then toluene (1.8 liters), water (1.8 liters) and sodium bicarbonate (49 g, 0.585 moles) was added and stirred. Layers were separated. The aqueous layer was back extracted with toluene twice (900 and 600 mL). All organic layers were combined and washed with water four times (1.8, 0.9, 0.9 and 0.9 liters). The organic layer was filtered and concentrated in vacuo. Heptane (750 mL) was added and solvents were removed again in vacuo. A heptane/toluene (85:15) mixture (2.45 liters) was added and heated until dissolution (about 65° C.). It was allowed to cool down slowly and it was seeded at 40° C. At 25° C. it was thick slurry. Then it was cooled to −12° C. and it was filtered. The cake was washed twice with heptane/toluene (85:15) mixture (200 mL). The solid was recrystallized from heptane/toluene (88:12) mixture (2.25 liters). The solid was washed twice with heptane/toluene (88:12) mixture (200 mL) and it was dried in a vacuum oven at 65° C. until constant weight. 152.1 g of Compound VI-a was obtained (81% yield).

EXAMPLE 6
Scheme 3, Synthesis of III-a from I-a.

Compound I-a (5 g, 0.022 moles) was dissolved in THF (50 mL) and cooled down to −48° C. sec-Butyllithium 1.3 M in cyclohexane (44 mL, 0.057 moles) was added at a rate that the temperature was below −37° C. The mixture was held at −43 to −39° C. for 1 hour. Cyclopropylacetinyl-trifluoromethyl ketone (4 g, 0.024 moles) was added at −48° C. and stirred for 40 minutes. Reaction was quenched with t-butyl methyl ether and water. The organic layer was washed with water and the solvent was removed in vacuo. The crude was stirred in 15 mL of cyclohexane. A solid precipitated which was filtered, washed and dried. 3.45 g of Compound III-a was obtained (41% yield).

EXAMPLE 7
Scheme 3, Synthesis of IV-a from I-a.

N-t-BOC-4-chloroanaline (Compound I-a) (5 g, 0.022 moles) was dissolved in THF (50 mL) and cooled down to −67° C. sec-Butyllithium 1.3 M in cyclohexane (42 mL, 0.055 moles) was added at a rate that the temperature was below −45° C. The mixture was held at −43 to −45° C. for ½ h. Cyclopropylacetinyl trifluoromethyl ketone (4 g, 0.024 moles) was added at −72° C. and it was allowed to warm up to room temperature over a period of 3½ hours. The mixture was heated to reflux (69° C.) and held for 1½ hours. It was then quenched with ethyl acetate and aqueous acetic acid. Layers were separated. The organic layer was washed with brine and the solvent was removed in vacuo. The crude was stirred in heptanes. A precipitate of Compound II-a was filtered and washed with heptanes; 2.9 g of Compound II-a was obtained (42% yield).

EXAMPLE 8
Scheme 3, Synthesis of IV-a from II-a.

N-Butyllithium (2.5M in hexanes, 2.85 mL, 0.0071 moles) was placed in a 100 mL round bottom flask and cooled to 0° C. THF (5 mL) was slowly added, then cyclopropylacetylene (0.51 g, 0.00773 moles). The mixture was cooled to −70 ° C. and a solution of compound II-a (1 g, 0.00309 moles) in THF (1 mL) was added. The mixture was allowed to warm up and it was heated to reflux (65° C.). After 2.5 h the reaction mixture was quenched with 0.5 M HCl (5 mL) and tert-butyl methyl ether (5 mL). The layers were separated and the top organic layer was washed with water and concentrated in vacuo. The residue was slurried in heptane and filtered to yield 0.68 g of compound IV-a.

EXAMPLE 9

Synthesis of Compound IV-a from N-ethyoxycarbonyl-4-chloroaniline.

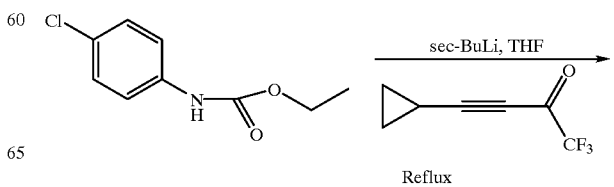

25
-continued

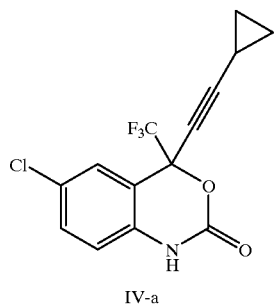

IV-a

N-ethoxycarbonyl-4-chloroaniline (0.44 g, 0.0022 moles) was dissolved in THF (5 mL) and the solution was cooled down to −50° C. sec-Butyllithium 1.3 M in cyclohexane (4.2 mL, 0.0055 moles) was added at a rate that the pot temperature was below −40° C. The mixture was then cooled to −56° C. cyclopropylacetinyl trifluoromethyl ketone (0.4 g, 0.0024 moles) was added. The mixture was allowed to warm up to room temperature and then it was heated to reflux (69° C.) and held for one hour. The reaction was quenched with ethyl ether (20 mL) and 2.5% aqueous acetic acid (20 mL). The organic layer was washed with 2.5% aqueous acetic acid, and then brine. The solvent was removed in vacuo to give 0.71 g of crude. A portion of the crude was slurried in hexanes and Compound IV-a was isolated as a solid (0.25 g).

EXAMPLE 10

Synthesis of Compound VII wherein in Formula (II) $R^1$ is ethoxycarbonyl

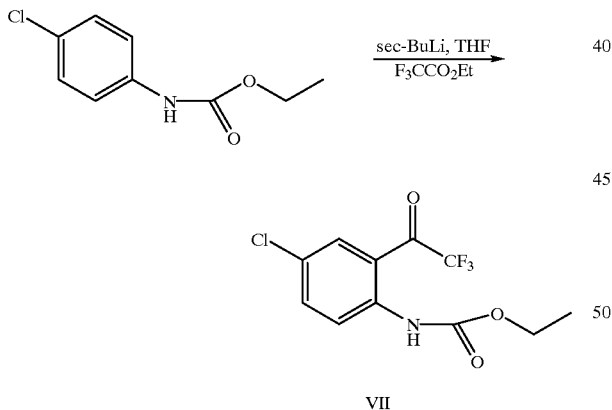

VII

N-Ethoxycarbonyl-4-chloroaniline (0.44 g, 0.0022 moles) was dissolved in THF (5 mL) and the solution was cooled down to −50° C. sec-Butyllithium 1.3 M in cyclohexane (4.2 mL, 0.0055 moles) was added at a rate that the pot temperature was below −40° C. The mixture was then cooled to −56° C. and ethyl trifluoroacetate (0.72 g, 0.0050 moles) was added. After 1 h 15 minutes, the reaction was quenched with t-butyl methyl ether (10 mL) and water (10 mL). The organic layer was washed twice with water (10 mL), and the solvent was removed in vacuo to give 0.31 g of crude Compound VII.

26
EXAMPLE 11

Synthesis of Compound IV-a from N-menthoxycarbonyl-4-chloroaniline

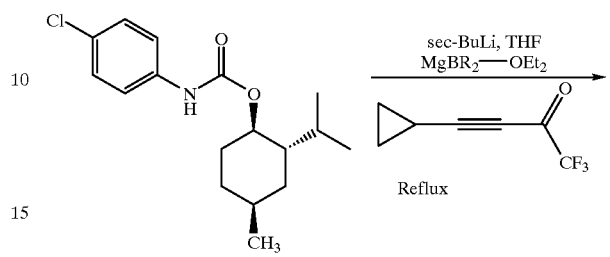

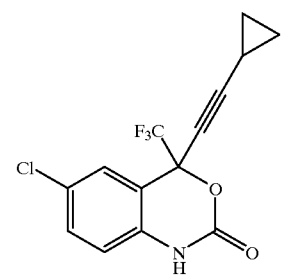

N-Menthoxycarbonyl-4-chloroaniline (0.68 g, 0.0022 moles) was dissolved in THF (5 mL) and the solution was cooled down to −50° C. sec-Butyllithium 1.3 M in cyclohexane (4.2 mL, 0.0055 moles) was added at a rate that the pot temperature was below −40° C. MgBr$_2$.OEt$_2$ (1.42 g, 0.0055 moles) was added and the mixture was then cooled to −75° C. Cyclopropylacetinyl trifluoromethyl ketone (0.4 g, 0.0024 moles) was added and after 3 hours isopropyl alcohol (0.08 mL) was used to quench the reaction. The mixture was heated to ref lux (72° C.) and held for three hours. The reaction was quenched with t-butyl methyl ether (20 mL) and NH$_4$Cl (20 mL). The organic layer was washed with NH$_4$Cl (20 mL) and then water and the solvent was removed in vacuo to obtain 1.1 g of crude. A portion of the crude was triturated in hexanes and Compound IV-a was isolated as a solid (0.45 g).

EXAMPLE 12

Synthesis of Compound IX wherein $R^1$ in Formula (III) is borneolcarbonyl

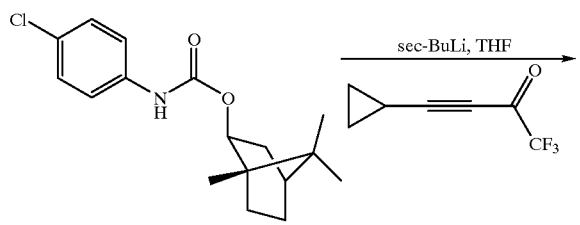

-continued

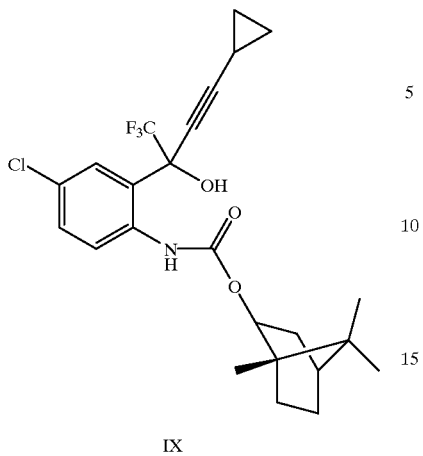

IX

N-Bornyloxycarbonyl-4-chloroaniline (0.71 g, 0.0022 moles) was dissolved in THF (5 mL) and the solution was cooled down to −50° C. sec-Butyllithium 1.3 M in cyclohexane (5 mL, 0.0065 moles) was added at a rate that the pot temperature was below −42° C. The mixture was then cooled to −48° C. Cyclopropylacetinyl trifluoromethyl ketone (0.4 g, 0.0024 moles) was added. The reaction was quenched with t-butyl methyl ether (10 mL) and 2.5% aqueous acetic acid (15 mL). The organic layer was washed with brine and the solvent was removed in vacuo to obtain 1.1 g of crude Compound IX as a mixture of diastereomers.

EXAMPLE 13

Preparation of 5-Chloro-α-n-butyl-α-trifluoromethyl-2-t-butoxycarbonylamino-benzenemethanol, Compound X.

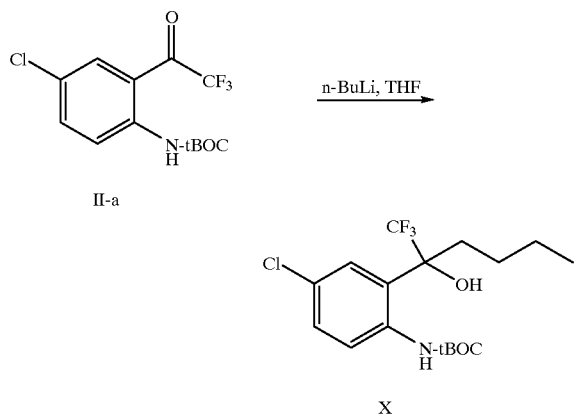

To a solution of Compound II-a (3.5 g, 10.8 mmol) in THF (10 mL) was added 2.5 N butyllithium (9.5 mL, 23.8 mmol) while maintaining the temperature below 30° C. After stirring 1 hour at ambient temperature, the solution was quenched with water (20 mL) and acetic acid (1 mL), then diluted with methyl t-butyl ether (10 mL). The organic phase was washed with saturated aqueous ammonium chloride (10 mL), dried with sodium sulfate and concentrated in vacuo to an oily solid which was recrystallized from 10 ML hexanes to give 2.2 g (54% yield) of Compound X. mp 162–163.5° C. $^1$H NMR (300 MHz, CDCl$_3$) δ 8.80 (brs, 1H), 8.12 (brd, J=9 Hz, 1H), 7.28 (dd, J=2, 9 Hz, 1H), 7.17 (brs, 1H), 2.36 (m, 1H), 1.90 (complex, 1H), 1.49 (s, 9H), 1.43–1.20 (complex, 4H), 0.90 (t, J=7 Hz, 3H).

EXAMPLE 14

Preparation of 5-Chloro-α-(5′-chloropropylethynyl)-α-trifluoro-methyl-2-t-butoxycarbonylamino-benzenemethanol, Compound XI.

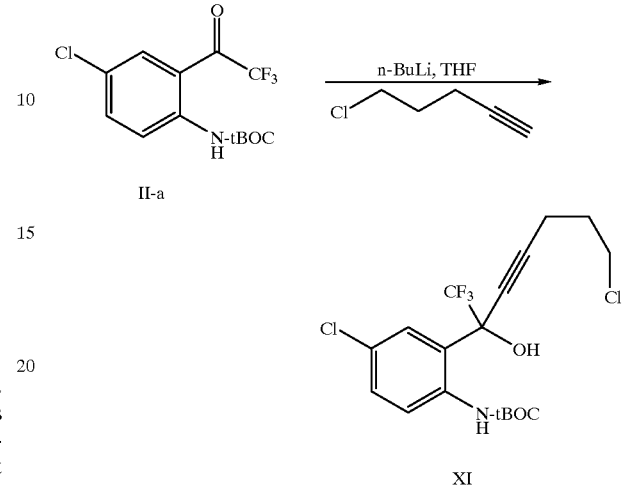

To a solution of 5-chloropentyne (2.4 g, 23.8 mmol) in THF (5 mL) was added 2.5 N butyllithium (9.5 mL, 23.8 mmol) while keeping the temperature below 25° C. The resulting solution was charged to a solution of Compound II-a (3.5 g, 10.8 mmol) in THF (10 mL) and the resulting slurry stirred at ambient temperature for 1 hour, then quenched with water (10 mL) and acetic acid (1 mL), then diluted with methyl t-butyl ether (10 mL). The organic phase was washed with saturated aqueous ammonium chloride (10 mL), dried with sodium sulfate and concentrated in vacuo to an oil which was recrystallized from 10 mL hexanes to give 2.7 g (59% yield) of Compound XI. mp 116–118° C.; $^1$H NMR (300 MHz, CDCL$_3$) δ 8.26 (brs, 1H), 8.06 (d, J=8 Hz, 1H), 7.66 (d, J=2 Hz, 1H), 7.33 (dd, J=2, 7 Hz, 1H), 3.68 (t, J=7 Hz, 2H), 3.58 (s, 1H), 2.60 (t, J=7 Hz, 2H), 2.07 (m, 2H), 1.50 (s, 9H).

EXAMPLE 15

Preparation of 6-Chloro-4-(5′-chloropropylethynyl)-1,4-dihydro-4-(trifluoromethyl)-2H-3,1-benzooxazin-2-one, Compound XII.

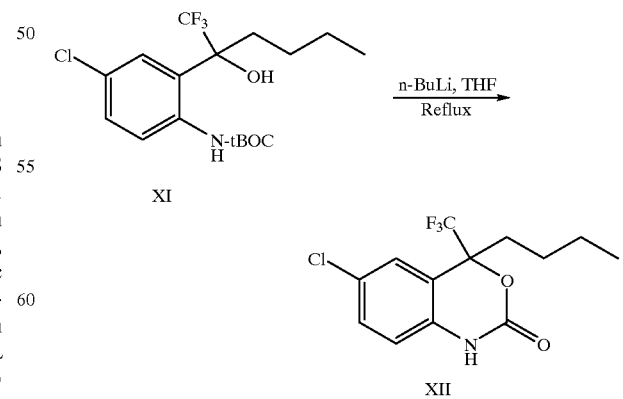

The compound prepared in Example 14 (0.43 g, 1.00 mmol) was dissolved in toluene (4 mL) and treated with 2.5

N butyllithium (0.4 mL, 1 mmol). The mixture was refluxed for 4 hours then cooled to room temperature. Dilute acetic acid/water (5 mL) was added and the phases separated. The organic phase was washed with three 5 mL portions of water, dried with MgSO$_4$ and concentrated in vacuo to an off-white solid which was recrystallized from hexane to give 260 mg (83% yield) of Compound XII. mp 138–140° C.; $^1$H NMR (300 MHz, CDCL$_3$) δ 9.95 (brs, 1H), 7.36 (dd, J=2, 8 Hz, 1H), 7.20 (d, J=2 Hz, 1H), 6.91 (d, J=8 Hz), 2.2 (m, 2H), 1.5–1.1 (complex, 4H), 0.92 (t, J=7 Hz, 3H).

EXAMPLE 16

Preparation of 6-Chloro-4-(n-butyl)-1,4-dihydro-4-(trifluoromethyl)-2H-3,1-benzoxazin-2-one, Compound XIII

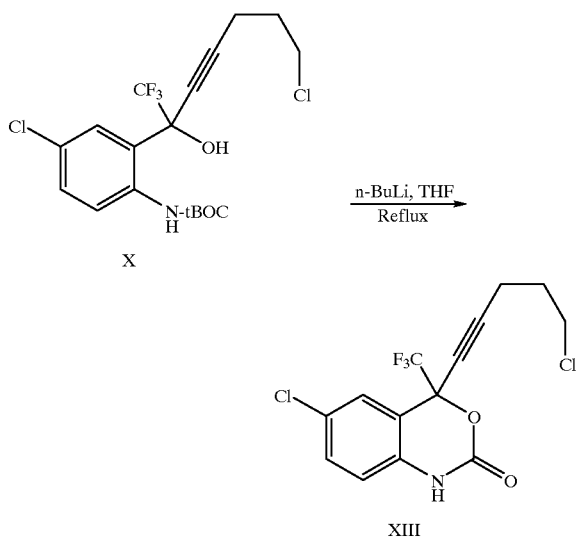

The compound prepared in Example 13 (0.76 g, 1.98 mmol) was dissolved in toluene (8 mL) and treated with 2.5 N butyllithium (0.8 mL, 2 mmol). The mixture was refluxed for 4 hours then cooled to room temperature. Dilute acetic acid/water (10 mL) was added and the phases separated. The organic phase was washed with three 10 mL portions of water, dried with MgSO$_4$ and concentrated in vacuo to an off-white solid which was recrystallized from hexane to give 450 mg (85% yield) of Compound XIII. mp 178–179° C.; $^1$H NMR (300 MHz, CDCL$_3$) δ 9.60 (brs, 1H), 7.48 (d, J=2 Hz, 1H), 7.37 (dd, J=2, 8 Hz, 1H), 6.90 (d, J=8 Hz, 1H), 3.66 (t, J=7 Hz, 2H), 2.60 (t, J=7 Hz, 2H), 2.05 (p, J=7 Hz, 2H).

EXAMPLE 17

Preparation of Trifluoromethyl cyclopropylethynyl ketone, Compound XV

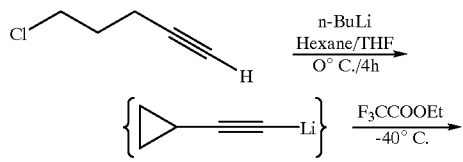

-continued

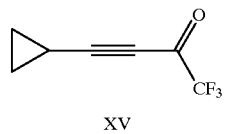

Synthesis (a)

To a solution of n-butyllithium in hexanes (2.5M, 1600 ml) at 0° C. under nitrogen was added THF (1600 ml). The mixture was cooled to −10° C. and neat 5-chloro-1-pentyne (201 gm) was added dropwise over 30 minutes while keeping the internal temperature between 0–5° C. The batch was aged at 0° C. for 3–4 hours, while the progress of the cyclization step was monitored by HPLC [Inertsil Phenyl column, CH3CN, water, phosphoric acid; gradient elution from 40:60:0.1 to 50:50:0.1 in 15 min, flow=1.0 ml/min, UV detection at 195nm]. The reaction was considered complete when the level of starting material was below 0.5 A%. Once the cyclization step was complete, the reaction was cooled to −50° C. To the resulting thin slurry was added neat ethyl trifluoroacetate (260 ml) over 30 minutes. The internal temperature was allowed to rise to −40° C. during the addition. The batch was aged at −50° C. for one hour and was quenched by the addition of 2N HCl (1500 ml). The layers were separated and the light yellow organic layer was washed with DI water (2×750 ml) and dried (Na$_2$SO$_4$). The batch was concentrated in vacuo (125 mm/25° C.) to afford a red oil. The batch was purified by fractional distillation through a 6" Vigreux column. The fration with a boiling range of 72–80° C./110 mm was collected as the product. Yield: 136.4 grams (43%) of the ketone (XV) as a light yellow oil.

In a Parallel Process: Synthesis (b)

N-Butyllithium (2.5 M, 800 mL, 2.00 mol) was cooled to −28° C. THF (800 mL) was slowly added, and then 5-chloro-1-pentyne (100 g, 0.98 mol) at a rate that the temperature was kept below 0° C. After 4 h at 0° C., the mixture was cooled to −55° C. and ethyl trifluoroacetate (180 mL, 1.09 mol) was added over a period of 1 h. After 1 h the mixture was cooled to −45 ° C. and quenched with 2N HCl (750 mL). The layers were separated and the organic phase was washed with water (750 mL), dried with Na$_2$SO$_4$ and concentrated in vacuo. The crude product was distilled under vacuum to yield 64.0 g (40%) of compound XV as a pale yellow oil: bp 76–79 ° C. (70 mmHg); $^1$H NMR (CDCl$_3$) d 1.55 (m, 1H), 1.05–1.20 (m, 4H); $^{13}$C NMR (CDCl$_3$) d 166.82, 114.68, 72.29, 67.95, 10.96, 0.25; IR (cm$^{-1}$) 2209, 1705, 1217, 1163, 1066, 920.

Pentafluoroethyl cyclopropylethynyl ketone, (XVI) can be synthesized in an analogous fashion using ethyl pentafluoropropionate in the above reaction.

Although the present invention has been described with respect to specific embodiments, the details of these embodiments are not to be construed as limitations. Various equivalents, changes and modification may be made without departing from the spirit and the scope of this invention, and it is understood that such equivalent embodiments are part of this invention. The present invention may be embodied in other specific forms without departing from the spirit or

What is claimed is:
1. A compound of the formula:
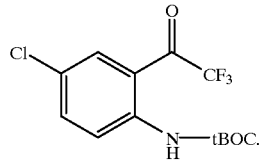
(II-a)
2. A compound of the formula:
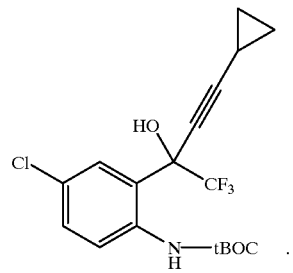
(III-a)
* * * * *